United States Patent [19]

Lewis et al.

[11] Patent Number: 5,795,292

[45] Date of Patent: Aug. 18, 1998

[54] METHOD FOR IMPROVING SIGNAL-TO-NOISE IN CLINICAL SPECTROMETRIC PROCEDURES

[75] Inventors: Gary D. Lewis, Grosse Pointe Farms; Wayne P. Messing, Troy; Oleg Gonopolskiy, Southfield; Richard S. Scheuing, Ann Arbor, all of Mich.

[73] Assignee: Somanetics Corporation, Troy, Mich.

[21] Appl. No.: 641,875

[22] Filed: May 2, 1996

Related U.S. Application Data

[62] Division of Ser. No. 324,120, Oct. 14, 1994, Pat. No. 5,697,367.

[51] Int. Cl.$^6$ .................................................. A61B 5/00
[52] U.S. Cl. ........................... 600/323; 600/310; 600/322
[58] Field of Search ........................... 128/633, 664–667, 128/639, 640, 901; 600/323, 473, 476, 310, 322

[56] References Cited

U.S. PATENT DOCUMENTS

| | | | |
|---|---|---|---|
| 2,790,438 | 4/1957 | Taplin et al. | 128/633 |
| 3,230,951 | 1/1966 | Teschner | 128/2.05 |
| 3,602,213 | 8/1971 | Howell et al. | 128/2.05 F |
| 3,769,974 | 11/1973 | Smart et al. | 128/2.05 |
| 3,810,460 | 5/1974 | Van Nie | 128/2.05 E |
| 3,814,081 | 6/1974 | Mori | 128/2 L |
| 3,822,695 | 7/1974 | Takayama | 128/2 L |
| 3,910,701 | 10/1975 | Henderson et al. | 356/39 |
| 4,013,067 | 3/1977 | Kresse et al. | 128/2.05 R |
| 4,015,595 | 4/1977 | Benjamin, Jr. | 128/2.05 |
| 4,063,551 | 12/1977 | Sweeney | 128/2.05 P |
| 4,091,803 | 5/1978 | Pinder | 128/2.05 P |
| 4,109,643 | 8/1978 | Bond et al. | 128/2 L |
| 4,163,447 | 8/1979 | Orr | 128/666 |
| 4,223,680 | 9/1980 | Jöbsis | 128/633 |
| 4,249,540 | 2/1981 | Koyama et al. | 128/666 |
| 4,259,963 | 4/1981 | Huch | 128/635 |

(List continued on next page.)

FOREIGN PATENT DOCUMENTS

| | | | |
|---|---|---|---|
| 646376 | 4/1993 | Australia. | |
| 2517129 | 6/1976 | Germany | 356/32 |
| 2076903 | 12/1981 | United Kingdom | 128/2 L |
| WO8909566 | 10/1989 | WIPO. | |
| WO9412096 | 6/1994 | WIPO. | |

*Primary Examiner*—Lee S. Cohen
*Attorney, Agent, or Firm*—Price, Heneveld, Cooper DeWitt & Litton

[57] ABSTRACT

A method of conducting clinical examination procedures by use of electrically actuated spectrometric apparatus, of the type which uses a sensor that is placed in contact with the patient to transmit and receive electromagnetic energy of selected wavelengths for non-invasive in vivo examination of a selected area on the body, in which a conductive member is placed in contact with the patient near or at the location of the sensor and connected to the signal-processing circuitry of the processor for the spectrometric signals in a manner such that the examination signals have significantly less noise content than would otherwise be true. In so doing, the signal-processing circuitry is isolated from the power supply circuitry, and the sensor and conductive member are preferably coupled to the processor by use of an isolation preamplifier, such that the signal-processing ground potential reference is maintained separate and distinct from the power supply ground. The specially-grounded conductive member that is placed in contact with the patient is preferably made part of the sensor itself, as by using a conductive material on at least part of the sensor surface that is placed in contact with the patient, and such a conductive surface element may comprise a flexible outer coating or layer of a compliant sensor which is conformable to the shape of the patient extremity to which it is applied. In this manner, the surface potential of the patient at the location of the sensor may be equalized with that of the signal-processing circuitry ground potential to substantially reduce signal noise content, and ambient sources of electrical noise may be effectively shielded as well.

14 Claims, 7 Drawing Sheets

U.S. PATENT DOCUMENTS

| | | | |
|---|---|---|---|
| 4,267,844 | 5/1981 | Yamanishi | 128/633 |
| 4,281,645 | 8/1981 | Jöbsis | 128/633 |
| 4,321,930 | 3/1982 | Jöbsis et al. | 128/633 |
| 4,332,258 | 6/1982 | Arai et al. | 128/666 |
| 4,336,809 | 6/1982 | Clark | 128/665 |
| 4,344,438 | 8/1982 | Schultz | 128/634 |
| 4,350,163 | 9/1982 | Ford, Jr. et al. | 128/633 |
| 4,380,240 | 4/1983 | Jöbsis et al. | 128/633 |
| 4,510,938 | 4/1985 | Jöbsis et al. | 128/633 |
| 4,515,165 | 5/1985 | Carroll | 128/664 |
| 4,570,638 | 2/1986 | Stoddart et al. | 128/665 |
| 4,685,464 | 8/1987 | Goldberger et al. | 128/633 |
| 4,763,660 | 8/1988 | Kroll et al. | 128/640 |
| 4,770,179 | 9/1988 | New, Jr. et al. | 128/633 |
| 4,805,623 | 2/1989 | Jöbsis | 128/633 |
| 4,819,752 | 4/1989 | Zelin | 128/633 |
| 4,825,872 | 5/1989 | Tan et al. | 128/633 |
| 4,825,879 | 5/1989 | Tan et al. | 128/633 |
| 4,830,014 | 5/1989 | Goodman et al. | 128/665 |
| 4,840,179 | 6/1989 | Ullrich | 128/633 |
| 4,865,038 | 9/1989 | Rich et al. | 128/633 |
| 4,867,557 | 9/1989 | Takatani et al. | 356/41 |
| 4,880,304 | 11/1989 | Jaeb et al. | 356/41 |
| 4,928,691 | 5/1990 | Nicolson et al. | 128/633 |
| 4,938,218 | 7/1990 | Goodman et al. | 128/633 |
| 4,964,408 | 10/1990 | Hink et al. | 128/633 |
| 5,057,695 | 10/1991 | Hirao et al. | 250/575 |
| 5,080,098 | 1/1992 | Willett et al. | 128/633 |
| 5,094,240 | 3/1992 | Muz | 128/633 |
| 5,099,842 | 3/1992 | Mannheimer et al. | 128/633 |
| 5,111,817 | 5/1992 | Clark et al. | 128/633 |
| 5,139,025 | 8/1992 | Lewis et al. | 128/665 |
| 5,140,989 | 8/1992 | Lewis et al. | 128/665 |
| 5,188,108 | 2/1993 | Secker | 128/633 |
| 5,209,230 | 5/1993 | Swedlow et al. | 128/633 |
| 5,217,013 | 6/1993 | Lewis et al. | 128/633 |
| 5,226,417 | 7/1993 | Swedlow et al. | 128/633 |
| 5,299,572 | 4/1994 | Chen et al. | 128/639 |
| 5,349,961 | 9/1994 | Stoddart et al. | 128/665 |
| 5,465,714 | 11/1995 | Scheuing | 128/633 |
| 5,477,853 | 12/1995 | Farkas et al. | 128/633 |
| 5,482,034 | 1/1996 | Lewis et al. | 128/633 |

METHOD FOR IMPROVING SIGNAL-TO-NOISE IN CLINICAL SPECTROMETRIC PROCEDURES

This application is a division of application Ser. No. 08/324,120, filed Oct. 14, 1994, now U.S. Pat. No. 5,697,367.

This invention relates generally to spectrometry methods and apparatus, and more particularly spectrophotometry; more particularly, the invention relates to biomedical or clinical applications of such technology, as exemplified by electro-optically-implemented non-invasive oximeters, especially cerebral oximeters used in human patient applications. More particularly considered, the invention relates to methods and apparatus for improving the signal quality, and hence the operational accuracy, of clinical biomedical spectrophotometric apparatus such as oximeters, in which wavelength-specific light is applied to a test subject at one point and resultant light intensity is detected at another such point after passing through a given volume of the test subject tissue and/or other biological substance within the particular such volume involved.

REFERENCE TO RELATED PATENTS AND APPLICATIONS

The general subject matter and environment of the present invention is related to prior applications Ser. No. 07/711,452 (filed Jun. 6, 1991), now U.S. Pat. No. 5,217,013, and Ser. No. 08/065,140 (filed May 20, 1993), which are commonly owned with the present invention. Also, but to a lesser extent, the present invention is related to copending application Ser. No. 08/006,705 (filed Jan. 22, 1993), and its prior related applications, as well as Ser. No. 08/069,096, (filed May 28, 1993), all of which are expressly incorporated herein by reference as fully as though set forth in their entirety.

BACKGROUND

Noninvasive devices for determining arterial blood oxygen saturation by using spectrophotometric procedures have been known and used for some time, and many different examples of such devices are commonly available and used in medical facilities such as hospitals and the like. Further, a noninvasive cerebral oximeter based on spectrophotometric technology, for noninvasively determining blood oxygen saturation levels on a regional basis within the brain has been developed heretofore by Somanetics Corporation of Troy, Mich., owner of the present invention. In the most basic sense, these devices all operate by introducing light of two or more selected wavelengths at a predetermined location on the patient and measuring the intensity of resulting light at one or more other reasonably close points, and then subjecting the detected intensity signals to extensive comparative analysis by digital computer based on the known differences of absorption between reduced and oxygenated hemoglobin for the different selected wavelengths of light which have been introduced.

In such apparatus, the sources of the selected light spectra introduced into the patient and the detectors for determining resultant intensities are typically implemented by use of light-emitting diodes ("LEDs") and photodiodes, which are mounted in a carrier device of one type or another, the resulting device typically being referred to as a "sensor". In the case of most arterial oximeters, such sensors are either flexible or somehow articulatable, so that they can wrap or otherwise extend around a given portion of the anatomy (e.g., finger, earlobe, etc.), to thereby locate the detector opposite the light source. In the case of the cerebral oximeter, however, the sensor is typically applied to the forehead of the patient, with the light source and detectors disposed laterally adjacent one another so that the light travels through the skin and underlying bone (skull), enters the brain, and is reflected back toward the detectors after traveling through the intervening brain tissue, and back out through the skull, skin, etc.

Accordingly, there are a number of significant differences between the conditions encountered in cerebral oximetry and those encountered in arterial oximetry, particularly in view of the fact that the separation distances between the light sources and detectors must of necessity be substantially greater in cerebral oximetry than in arterial oximetry, since this distance is directly related to the effective depth which the interrogating light spectra travel through the patient and, in order to access (traverse) brain tissue rather than mere boundary layers of skin, bone, etc., this distance is substantially greater in cerebral oximetry than it is in arterial oximetry. Each increment of distance between the source LEDs and detectors significantly reduces the light intensity available at the detectors, however, and in fact it has been found that each centimeter of such spacing causes resultant light intensities at the detectors to be attenuated by a factor of ten. As a result of the necessarily greater separation distances required in cerebral oximeters, the detected light intensities are very small, and they produce detector outputs which are on the order of picoamps. In comparison to typical arterial oximeters, the detector output signals in cerebral oximeters can be of an order of magnitude which is perhaps one hundred times less.

These very small detector outputs encountered in cerebral oximetry therefore create far greater problems with respect to accurate analysis than is true of arterial oximeters, in particular pulse oximeters; in fact, the detector output signals can be so small in cerebral oximeters that they are sometimes lost in the electrical noise that is inherently present in such apparatus, particularly in the operating environment and the many different specific patient conditions encountered. Of course, when this condition exists, it is impossible to calculate any meaningful oxygen saturation values, and even where this is only partially true the accuracy of any values so produced will inherently be highly suspect. In this regard, typical patient environments where cerebral oximeters are most necessary include trauma centers and operating rooms, and it has been found that these environments usually include equipment that produces extensive amounts of electro-magnetic interference (EMI) and/or radio frequency interference (RFI). For example, electrocautery equipment typically used in operating room environments products extensive RFI, and does so at a location very near the oximeter sensor. While various filtering techniques can be utilized in an effort to reduce the effects of such noise, the problem encountered is extremely difficult to even deal with effectively, and essentially impossible to overcome, by using such measures.

SUMMARY OF THE INVENTION

The present invention recognizes certain basic attributes of the problem referred to in the preceding paragraphs, and provides methods and apparatus for essentially overcoming the same in an effective, relatively simple, and economically advantageous manner, by which spectrophotometric oximeter signal-to-noise ratio is improved by a factor of on the order of ten times.

More particularly, the invention recognizes that the operating room noise referred to above is or can be conducted through a patient and actually detected by the sensor, and that in a particular sense this noise can be effectively eliminated or substantially reduced by in effect establishing an electrical path between the patient and a portion of the oximeter control and actuation apparatus, so that the surface potential of the patient is directly linked (tied) to a reference potential having a known and predetermined value, while at the same time isolating and insulating the patient from all other excitation levels and conductive paths communicating with the oximetry apparatus.

Accordingly, in accordance with the invention, a novel concept is provided along with preferred implementations of such concept, by which the signal-to-noise ratio present in the photodetector outputs which are fed back for analysis are very substantially and significantly improved, by orders of magnitude, in a simple and effective manner.

More particularly considered, the invention provides an oximeter sensor structure which provides an effective conductivity path directly from the patient-contacting surface back to a predetermined point in the detector output signal-conducting path, in particular, the floating ground established in the detector circuitry. Most effectively this is done by actually making the sensor body conductive in at least the area immediately adjacent the detectors, so that the related surface area on the patient reflects this controlled potential and any such noise otherwise present is conducted away without contaminating the detector output. Other types of conductive members could also be utilized in accordance with the invention, including a separate electrode incorporated in a strap or the like for example.

In addition to the foregoing, the invention provides novel and effective implementations for signal-conducting path referred to above, which cooperate with the sensor configuration in providing the substantial noise reduction and improved signal level noted, while at the same time providing greater safety for the patient by increased isolation of other electrical circuits and componentry.

The foregoing principal objectives and advantages of the invention, together with other such objectives and advantages, will become more apparent after consideration of the ensuing description of preferred embodiments taken in view of the appended drawings.

INFORMATION FROM RELATED
APPLICATIONS AND PRIOR ART

Figure 1:
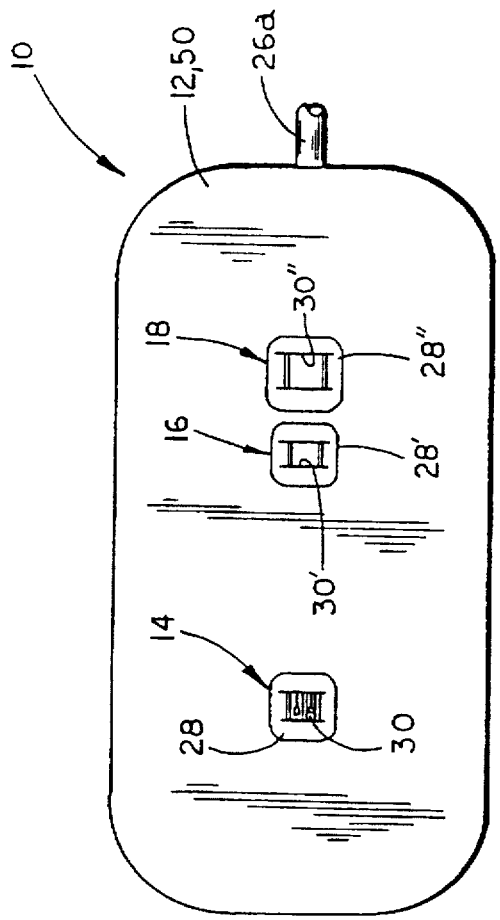
FIGS. 1 and 2 are top and sectional side elevational views, respectively, taken from the above-referenced copending application Ser. No. 08/273,366, showing the basic overall structure of a preferred form of sensor for a cerebral oximeter, exemplifying the environment of present invention as well as a preferred implementation thereof.
Figure 2:
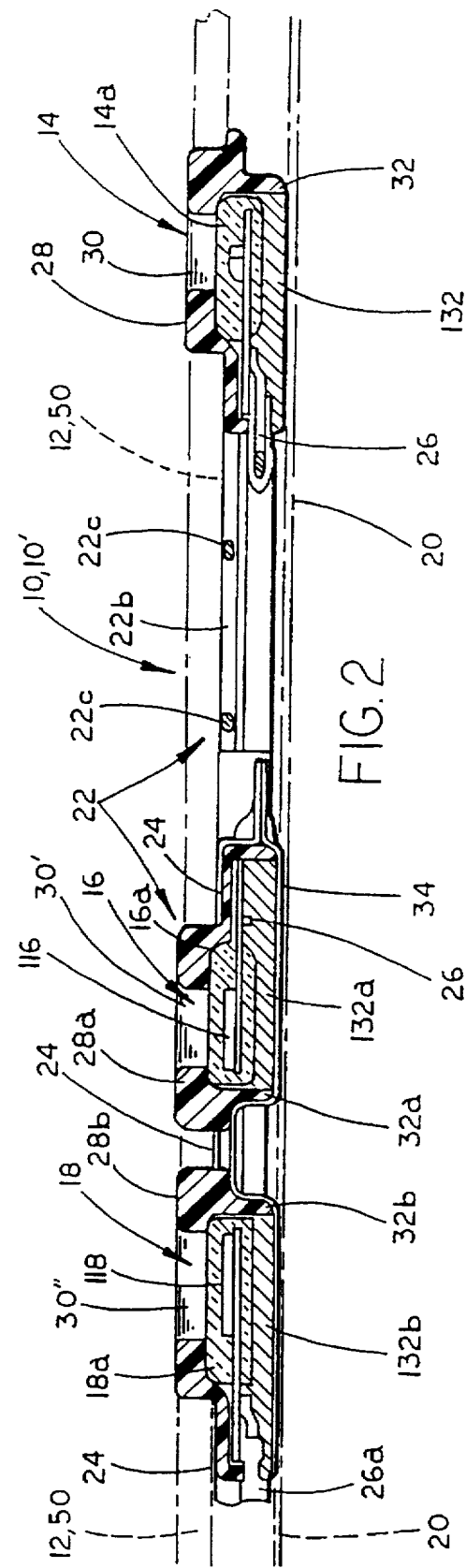

As indicated above, related and commonly-owned applications Ser. Nos. 08/060,853 and 08/065,140 (and its continuation application Ser. No. 08/273,366) illustrate and describe the structure and operating environment of "sensor" devices for use in optical cerebral oximeters such as that toward which the present invention is particularly directed, notwithstanding its broader aspects and more extensive potential applications, and FIGS. 1 and 2 are taken directly from the latter such application, with the same numbering retained. While these prior related applications are incorporated herein by reference as fully as though set forth herein and therefore need not be specifically repeated, it is pointed out for convenience that in the sensor 10 of FIGS. 1 and 2, the light sources (grouped LEDs) are designated generally by the numeral 14, the "near" and "far" detectors of the preferred oximeter embodiment are designated 16 and 18, respectively, and the interconnecting electrical conductors communicating between sensor 10 and the oximeter apparatus via a shielded cable 26A. Of particular relevance to the present application is a softly resilient outer patient-contacting pad or cover 12, which in these prior applications is implemented by use of the open-celled polymeric foam material known as "Poron". The outermost side of the pad or cover is coated with a suitable medical-grade adhesive, by which the sensor is securely but temporarily attached to the forehead of the patient during use. As disclosed in these related prior applications, a preferred such adhesive is a medical grade acrylic transfer adhesive made by Minnesota Mining and Manufacturing Company ("3M"). It is important to note that, in this prior implementation, both the outer pad 12 and its adhesive coating are non-conductive electrically, since prior thinking and accepted practices were to make every effort to insulate the patient from direct contact with any electrically-conductive element, to thereby avoid any inadvertent contact with electricity.

DESCRIPTION OF PREFERRED
EMBODIMENTS

Figure 3:
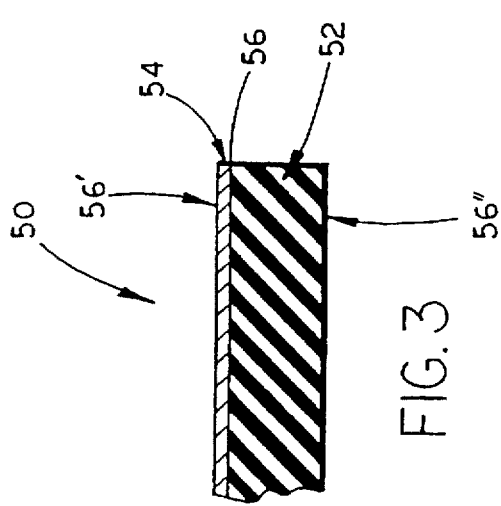
FIG. 3 is an enlarged fragmentary sectional side elevation depicting a preferred embodiment of the outer layers of a sensor in accordance with the invention.

While the overall structure of the sensor 10' in accordance with the present invention is preferably the same in most respects as that illustrated in FIGS. 1 and 2 (and described in the referenced and incorporated copending application Ser. No. 08/273,366), a marked difference exists in the nature of the outer pad 12, which is illustrated in FIG. 3 and designated herein by the numeral 50. In this respect, the non-conductive outer pad 12 of the prior embodiment described in the related application identified above and its non-conductive adhesive coating are replaced by a composite structure comprised of electrically conductive elements. Thus, the outer pad or cover 50 of the present invention (which is to replace the pad 12 of the prior embodiment) preferably comprises a layer 52 of resilient material of an electrically conductive nature, for example conductive neoprene rubber, and an adjacent layer of copper tape 54 adhesively secured thereto. Each side of resilient layer 52 is coated with a thin layer of conductive adhesive 56, whereby the outermost such layer (designated 56'), which contacts the patient, will securely affix the entire sensor thereto, while the innermost such layer (designated 56"), which contacts the other part of the sensor body and in particular the shielding material (designated by the numeral 24 in FIGS. 1 and 2 and essentially surrounding the detectors 16 and 18 except for their light-passage openings) will securely fasten the pad or cover 50 thereto in a completely conductive manner. Accordingly, a direct connective path is established from the forehead of the patient to the control and actuating circuitry of the oximeter (depicted generally in FIG. 4 and described hereinafter) through cable 26A.

In accordance with the invention as presently contemplated, the conductive neoprene layer 52 preferably comprises commercially available conductive Polychloroprene having a durometer of about 65 (plus or minus 5), Shore A (RDI formula #RD136A). The "copper tape" layer 54 preferably comprises the product known as "Flexshield 8016" sold by Adhesives Research, Inc. of Glen Rock, Pa., which combines a copper-impregnated rip-stop nylon material (available from Monsanto Company and designated as "Flectron") with a homogeneously conductive adhesive sold by Adhesives Research, Inc. under the designation "EC-2". The conductive adhesive 56 preferably comprises the product sold by Adhesives Research, Inc. under the trademark "ARclad 8006", which comprises an unsupported, self-wound transfer adhesive featuring the aforementioned "EC-2" pressure-sensitive conductive adhesive. No doubt, other such materials and other particular structural layups or arrangements may also be utilized, but these particular materials and the particular structure described comprise the most preferred embodiment and best mode presently contemplated.

With respect to the selected materials and components of the pad 50, it is important that conductivity be relatively high in a lengthwise direction (Z axis), as well as through their thickness. The conductive layer 54 is principally included to enhance (increase) conductivity between the patient and the other components, and particularly to make the entire relevant sensor area an effective conductor. In this regard, the preferred components (materials) noted above exhibit excellent adhesion qualities and conductivity; for example, the preferred adhesive 56 has a volume resistance of less than five ohms per square inch and a surface resistance of approximately 30K ohms per square centimeter, with fast static dissipation and a low Z-axis resistance. Similarly, the conductive layer 54 incorporates a very favorable adhesion characteristic and excellent conductivity while at the same time providing additional and significant shielding properties (more than 102 db at 100 KHz), while at the same time being highly flexible and readily conformable to adjacent surfaces. Examples of preferred thicknesses of these components are, for layer 52, 0.034 inch, plus or minus 0.012, for the "copper tape" layer 54, approximately 0.004 inch, and for the conductive adhesive layers 56, approximately 0.001 inch. As will be understood, a releasable liner (not specifically shown) should be used on the outside of layer 56' to facilitate handling of the pad and sensor, such liner being removed just prior to use of the sensor. It is to be noted that in addition to the qualities indicated above, the materials just identified provide desirably low or negligible primary skin irritation and sensitization, and the preferred adhesive passes FDA cytotoxicity testing.

Figure 4:
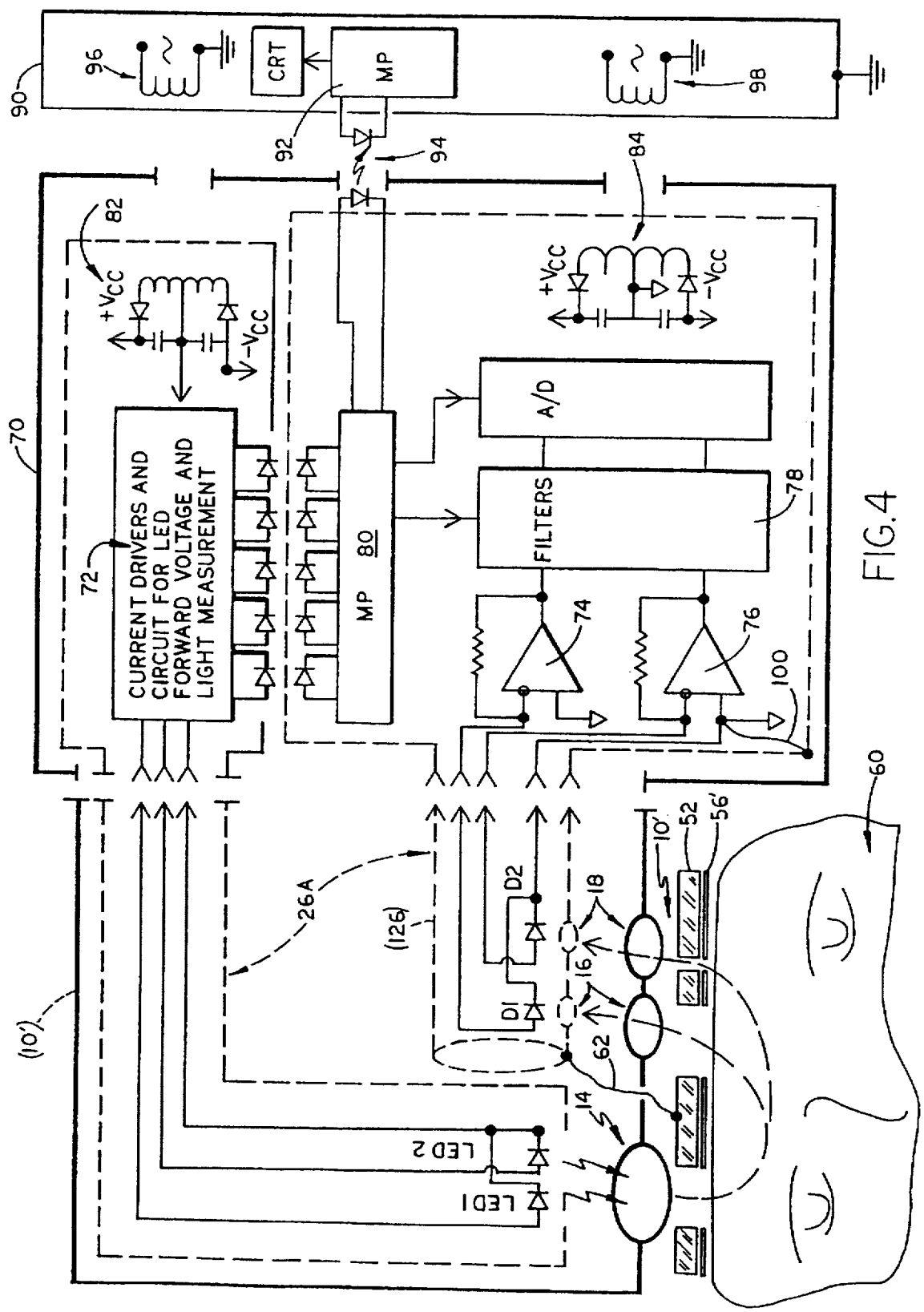
FIG. 4 is a fragmentary, pictorialized schematic representation depicting the application of the sensor to the t subject and presenting a block diagram of the related electrical circuitry.
Figure 4A:
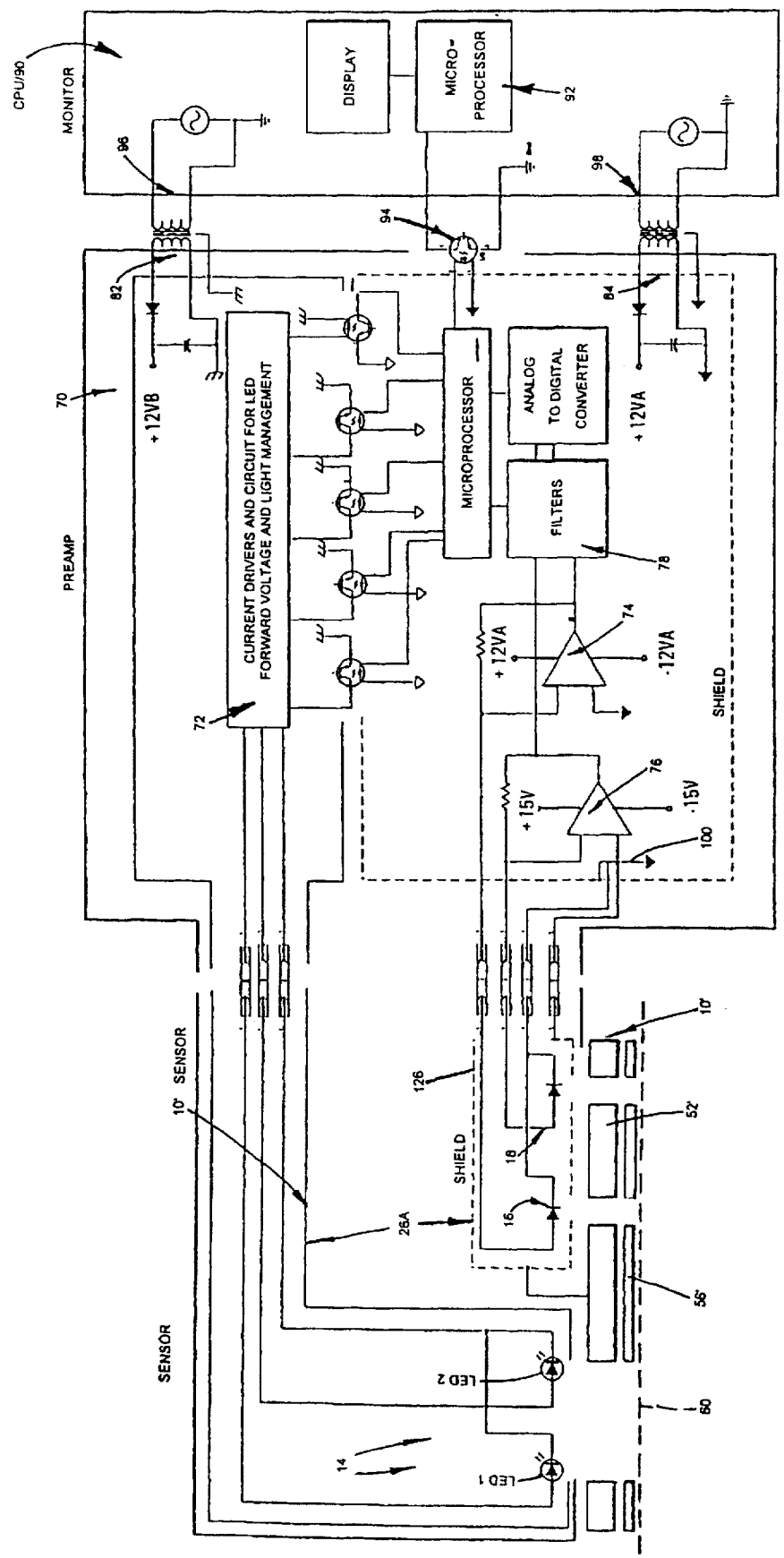
FIG. 4A is a counterpart of FIG. 4, drawn by use of a more formal convention.

While the basic structure and use of the sensor 10' in accordance with the present invention is consistent with that described in the related copending applications referenced above and incorporated herein by reference, the general arrangement and particular new aspects thereof are illustrated in FIG. 4. As seen there, the new type of sensor 10' incorporating the conductive patient interface pad or cover 50 is secured directly to the forehead of the patient 60 by the outermost adhesive layer 56' and, as indicated above, the sensor 10' is electrically coupled by the cable 26A back to the control and actuation components of the oximeter itself, designated in FIG. 4 as the "CPU/Monitor" 90, with an in-line preamp 70. In this general connection, it will be noted that FIG. 4 symbolically illustrates the direct electrical connection between the elastomeric layer 52 and the shielding componentry 24 of sensor 10' and cable 26A by a physical conductor 62, although in fact this conductor comprises the conductive layers themselves, including the adhesive layers 56.

While the general nature and operation of the oximeter itself is described in the various copending and incorporated applications, and the general nature and the components of the preamp 70 and "CPU/Monitor" 90 will be readily understood by those skilled in the art, especially in light of the incorporated disclosures, particular attributes of these are briefly commented upon here. In this regard, it is particularly pointed out that the "CPU/Monitor" 90 is effectively isolated from the preamp 70, and that the light source 14 (LED1 and LED2) its associated current drivers etc. 72 is isolated from the detectors 16 and 18, (comprising the photodiodes DI and D2 and interconnected circuitry, including amplifiers 74, 76, filters 78, etc.) Further, the microprocessor 80 incorporated in preamp 70 is coupled to its operationally-related microprocessor 92 of the central processing unit 90 by an optical pair 94, thereby avoiding all conductive paths which otherwise would exist therebetween.

In addition, it should be noted that the current drivers etc. 72 of preamp 70 have their own separate power supply transformer winding 82, and the same is true of the detector circuit, which has its own supply transformer winding 84, preamp supply transformer 82 being inductively coupled to a corresponding separate primary winding 96 of the CPU 90, and detector supply transformer 84 being inductively coupled to a separate CPU primary winding 98. It will be recognized that the arrangement just described provides essentially complete isolation of the different major components and operational component groupings from one another. In this arrangement, the patient 60 is effectively directly coupled to sensor 10' and the conductive path 62 to the shielding 24 and cable 26A, and the latter is directly coupled to the signal ground of the detector network (but isolated from, the power ground of the light source and electrical supplies). Thus, the patient 60 is in effect maintained at the same electrical potential as the signal ground of the detector circuitry in preamp 70, which is a floating ground not equatable with the earth ground of the power circuitry. In this manner, the extensive environmental noise of operating rooms, trauma centers, etc., as referred to above, is effectively eliminated or at least very substantially reduced, with results which are graphically illustrated in FIGS. 5–8 inclusively.

Figure 5:
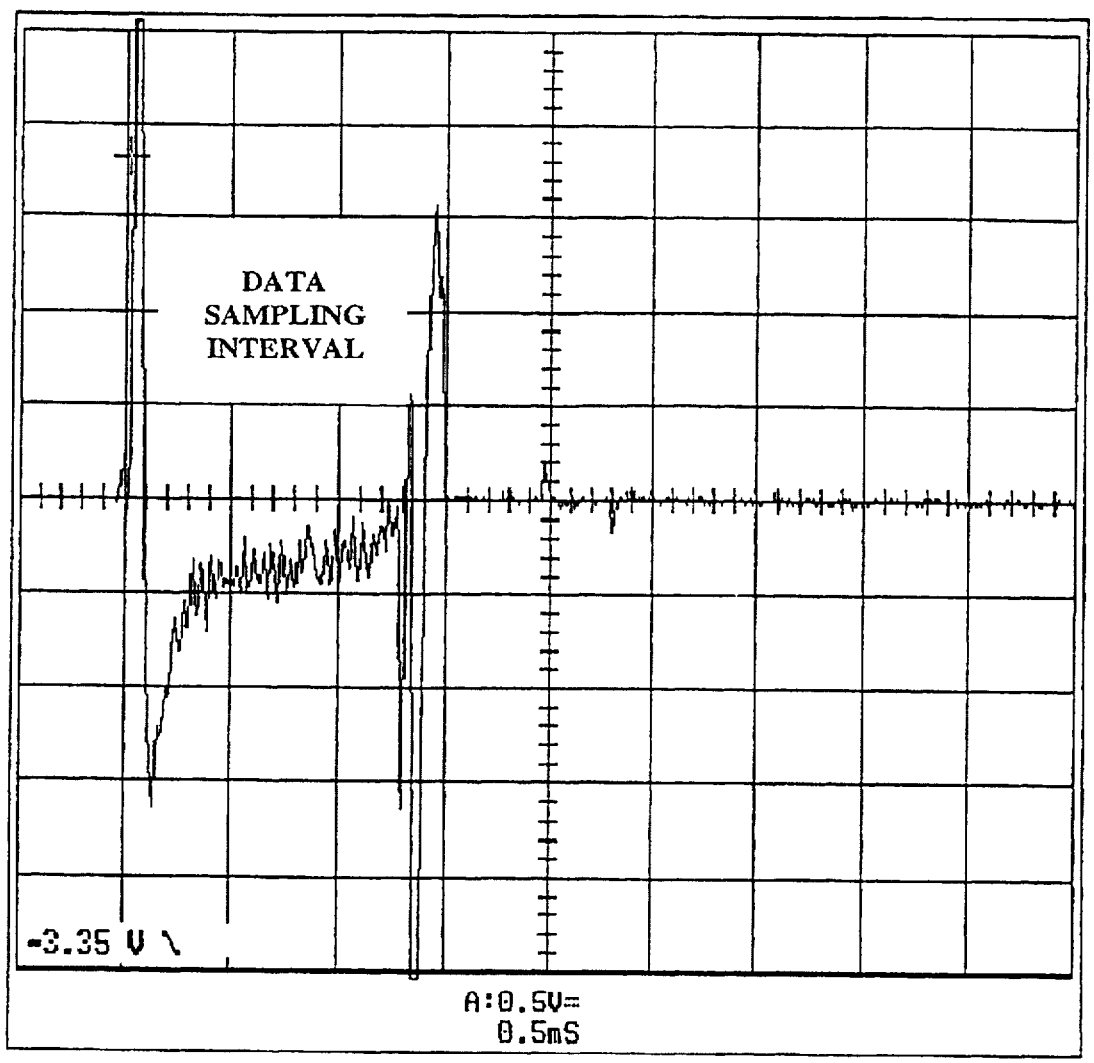
FIGS. 5–8 are graphical representations of the detector output wave shapes under various conditions, as labeled, illustrating the actual operational conditions involved in practice of the invention.
Figure 6:
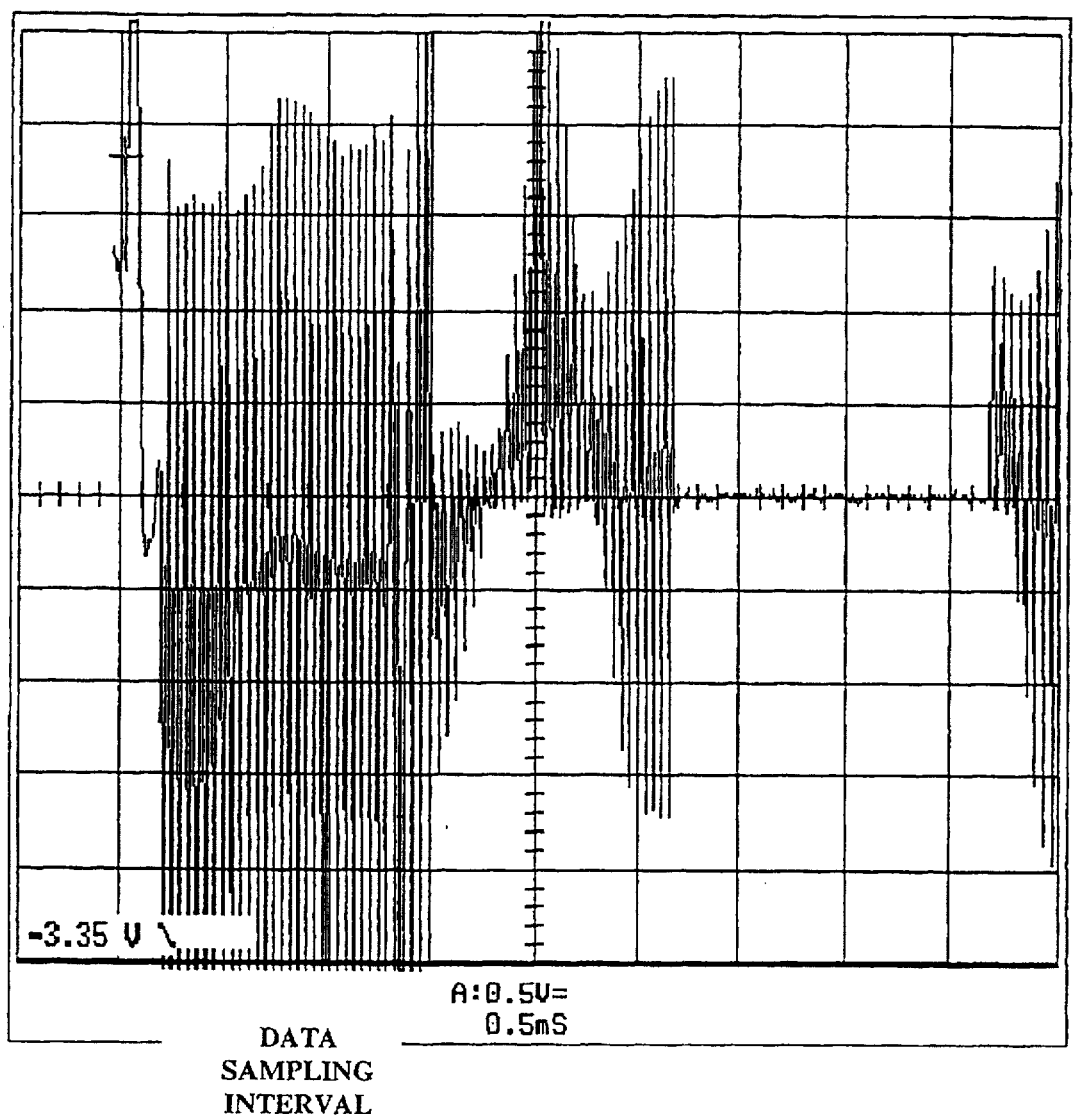

With more particular reference to FIGS. 5–8 each such graph constitutes a closely representative depiction of the amplified output of the photodiodes D1 and D2 comprising detectors 16 and 18, i.e. the output of amplifiers 74 and 76 (FIG. 4), taken during a time span which includes a particular data sampling interval (as designated) which, it should be noted, is longer in duration than the actual period during which source LED1 and LED2 are pulsed. Further, each different FIGS. 5–8 inclusive represents a particular set of conditions, as labeled. Thus, FIG. 5 represents a "nonconductive sensor" such as that taught in incorporated copending applications Ser. No. 08/065,140 and 08/273,366 and depicted in FIGS. 1 and 2, operating without an electrocautery noise source (all such graphical figures having the same coordinates in magnitudes, as labeled, i.e., the ordinate units representing 0.5 volts and the abscissa representing 0.5 milliseconds). As illustrated in FIG. 5, under these conditions the signal output 110 constitutes a relatively noisy but reasonably distinctive pulse which starts from a spike of about 1.5 v. and declines toward zero, with an average magnitude of perhaps 0.3/0.4 v. This graphical representation should be compared to that of FIG. 6, depicting the corresponding output from the same sensor configuration during a time when the electrocautery noise source is in operation. The nature and extent of the differences are clearly self-evident; i.e., the burst of FIG. 6 has extensive noise effects which in essence obscure the data signal and which would clearly make analysis difficult at best.

Figure 7:
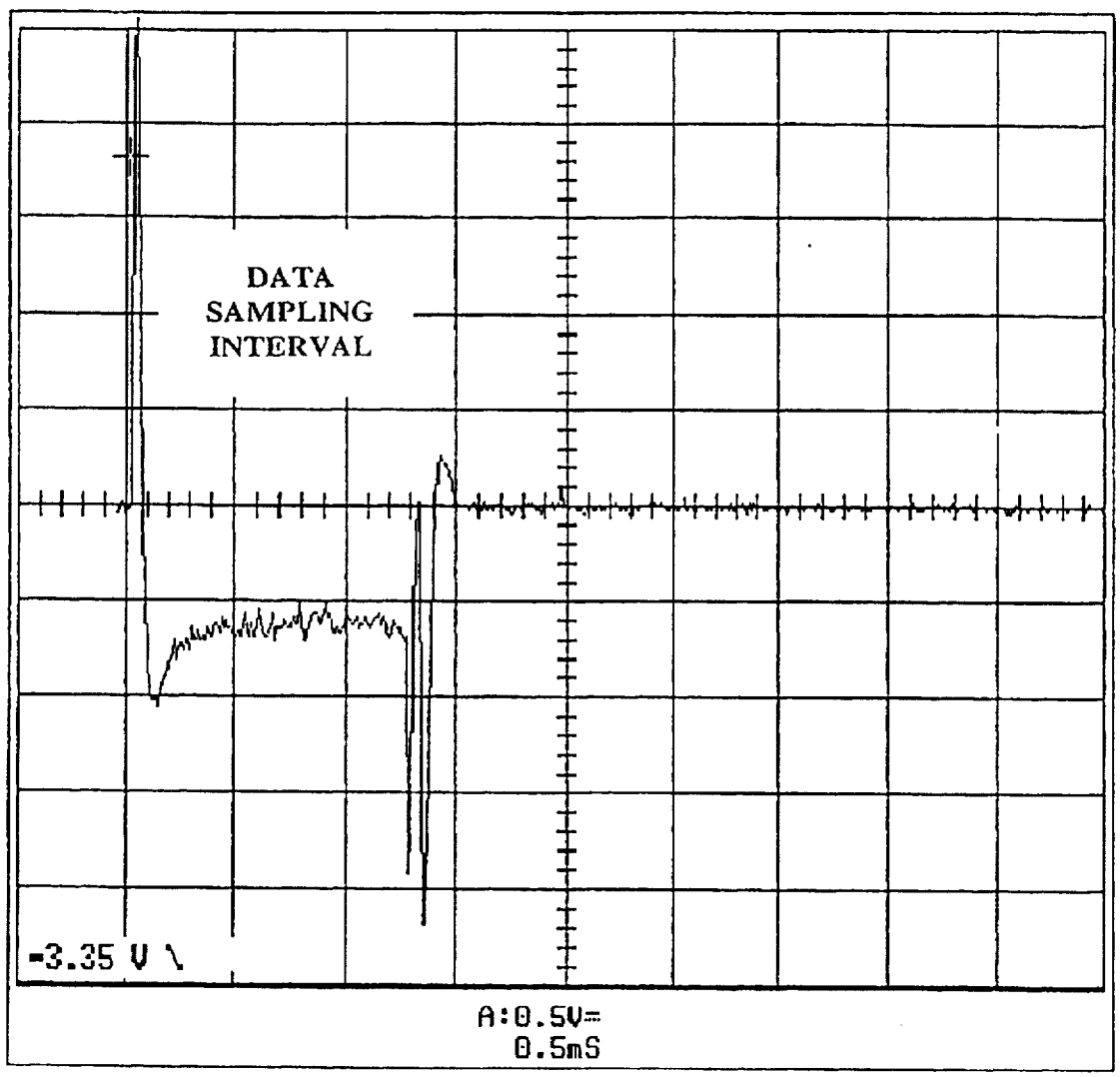
Figure 8:
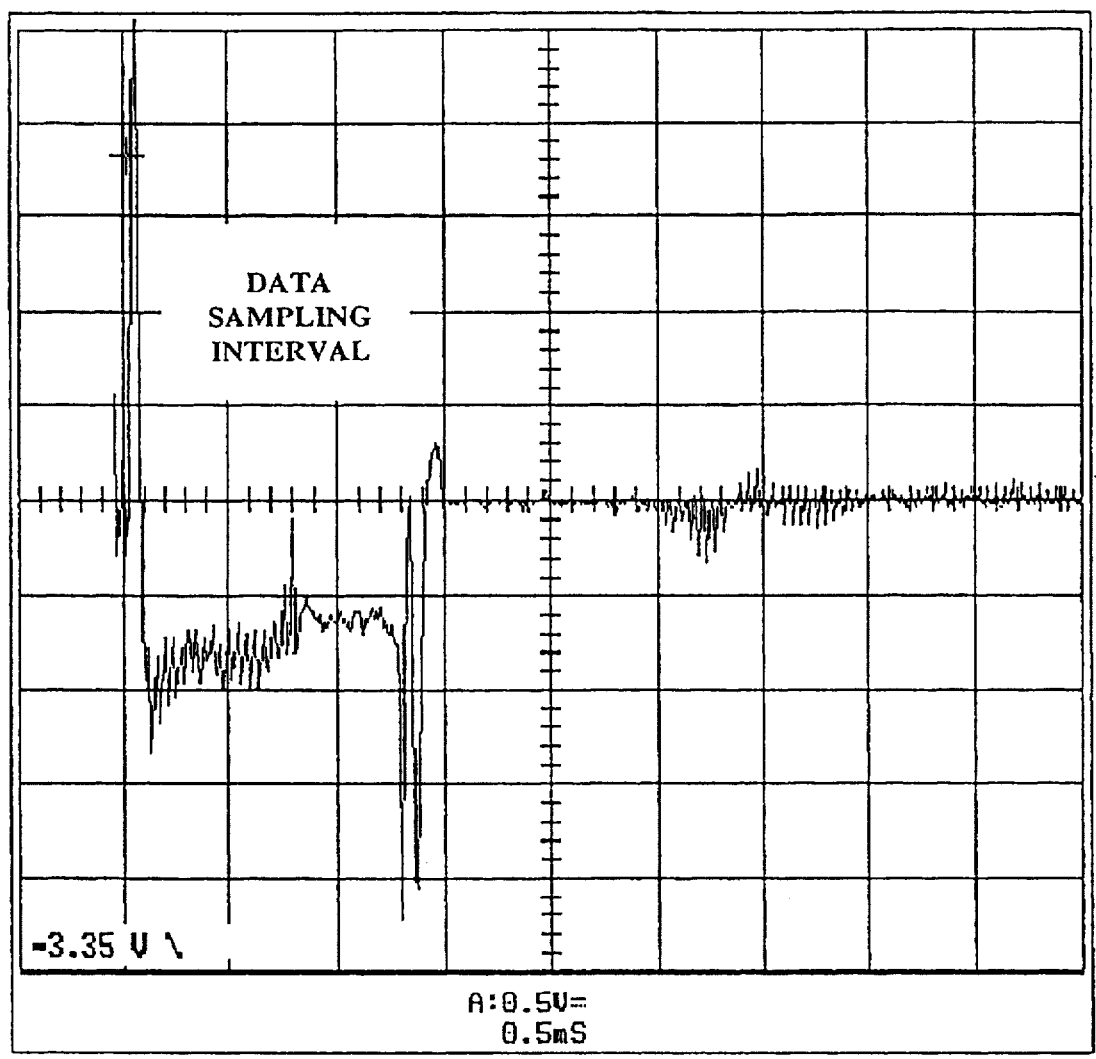

In contrast to the showings of FIG. 5 and FIG. 6, FIGS. 7 and 8 show the very different results obtained under the same circumstances with a conductive sensor 10' incorporating a conductive pad 50 in accordance with the present invention. As there shown, the detector output signal burst 220, 220' is much cleaner and well-defined, with minimal noise content. In fact, the burst 220' of FIG. 8, taken with an electrocautery knife in operation, is actually cleaner than the burst 110 of FIG. 5, which was taken without the electrocautery in operation. Furthermore, the bursts 220 and 220' of FIGS. 7 and 8 are very similar to each other, i.e., the presence or absence of electrocautery operation making little difference.

The graphical representations of results provided in FIGS. 5–8 inclusive are in fact representative, and certainly not idealized. In actual testing, the results provided by the invention are shown to improve the detector output signal-to- noise ratio by a factor of about 10 times. As will be readily understood, the significance of this improvement is both surprising and highly meaningful, clearly evidencing a very substantial improvement in operating accuracy which is of utmost importance to the overall performance, accuracy and acceptability of the oximeter itself.

It is to be pointed out that the improvement referred to above, while resulting in large part from the conductive path extending from the surface of the test subject (patient) to the preamp 70 by the conductive sensor 10', this implementation and result is itself enabled and substantially enhanced by the provision of the isolated preamp implementation shown and described in FIG. 4, since it would not be acceptable or advisable to merely connect the patient to a non-isolated path or ground conductor, especially not the earth ground used in the power circuitry. Additional benefits are also obtained by this isolation, in the form of improved accuracy and reduced noise, distortion, etc. With this point in mind, however, it should be appreciated that there are or may be entirely viable alternative measures for implementing the underlying concept, i.e., in addition to or instead of the conductive sensor implementation shown and described, and this concept should be born in mind in considering the scope of this patent and its appended claims.

It is to be pointed out once again that while the foregoing disclosure addresses a particular preferred embodiment, and best mode, the particular apparatus described and the various detailed aspects thereof noted are regarded as pertaining to only the most preferred version of the invention and to merely illustrate the principles and concepts involved in the invention, other embodiments and versions of the invention no doubt being feasible and potentially appropriate in other circumstances. It is therefore to be understood that the foregoing description of a particular preferred embodiment is provided for purposes of description and illustration, and not as a measure of the invention, whose scope is to be defined solely by reference to the ensuing claims. Embodiments of the invention differing from those set forth above which nonetheless utilize the underlying concepts of the invention and incorporate its spirit should therefore be considered as within the scope of the claims appended below, unless such claims by their language specifically state otherwise.

The embodiments of the invention in which an exclusive property or privilege is claimed are defined as follows:

1. A method of conducting clinical patient examinations by spectrometric apparatus, comprising the steps:

placing an electrically actuated sensor in contact with the patient for receiving and transmitting selected energy wavelength signals between the sensor and the patient;

coupling the sensor to an electrically powered controller and processor having electrical power circuits which are electrically isolated from at least portions of signal-processing circuits thereof to transmit patient examination signals to said signal-processing circuits; and electrically coupling at least a selected surface portion of said patient to said portions of said signal-processing circuits of said controller and processor which are electrically isolated from said power circuits thereof, to thereby establish and maintain substantially the same electrical potential between said selected surface portion of said patient and said portions of said processing circuits to which said selected surface portion is coupled and thereby substantially reduce the electrical noise content of said examination signals transmitted from said sensor to said processor.

2. The method set forth in claim 1, wherein said step of electrically coupling at least a selected portion of said patient to said signal-processing circuits is done by placing an electrically conductive member in direct physical contact with a selected surface area of the patient.

3. The method set forth in claim 2, wherein said step of electrically coupling is done by embodying said conductive member in said sensor and applying said sensor to said patient with said conductive member disposed in contact with the surface of said patient.

4. The method set forth in claim 3, wherein said electrically conductive member is embodied in a softly compliant outer layer of said sensor arranged for yieldable direct contact with the patient.

5. The method set forth in claim 2, wherein said signal-processing circuits have a signal ground potential reference and said step of electrically coupling is additionally done by electrically connecting said conductive member from said patient to the signal ground potential reference of said signal-processing circuits.

6. The method set forth in claim 2, wherein said electrically conductive member is secured in place against said patient by using electrically conductive adhesive therebetween.

7. The method set forth in claim 1, including the step of electrically isolating the electrical power circuits of said controller and processor from the signal-processing circuits thereof by connecting an isolation preamp having isolated power and signal-processing paths between said sensor on the one hand and said controller and processor on the other hand.

8. In a method of conducting clinical patient examination by use of electrically operated spectrometric apparatus of the type which transmits selected energy wavelengths to the patient for examination purposes and receives corresponding examination signals back from the patient, the improvement which comprises the step of placing an electrically conductive member in contact with a selected surface area of the patient, and using said conductive member to maintain at least said selected area of said patient at a predetermined electrical potential, to thereby substantially reduce the amount of electrical noise otherwise present in the examination signals received from the patient.

9. The improved method according to claim 8, wherein said examination signals have a signal ground potential reference and said electrically conductive member placed in contact with the patient is used by connecting it electrically to said ground potential reference for said examination signals.

10. The improved method according to claim 9, wherein electrical power circuits of said apparatus have a ground potential reference, and including the step of isolating said examination signal ground potential reference from said electrical power circuits ground potential reference.

11. In a method of conducting clinical patient examinations by spectrometric procedures in which selected energy wavelength signals are transmitted to the patient and resulting examination signals are received and coupled to an electrically powered processor having signal-processing circuits and electrical power circuits, for processing said clinical patient data, the improvement comprising the steps of:

using a sensor disposed in contact with said patient to transmit said energy wavelength signals thereto and receive said examination signals by electrically actuated components physically associated with said sensor;

electrically coupling said electrically actuated components to said processing circuits of said processor, for transmittal and receipt of said energy signals and said examination signals therebetween;

placing an electrically conductive member in contact with said patient, and establishing an electrically conductive path between said conductive member and said processor, whereby the electrical potential of said patient in the area contacted by said conductive member may be accessed; and electrically isolating said conductive member and conductive path from the electrical power circuits of said processor, and establishing and maintaining substantially the same electrical potential between said conductive member and at least portions of said signal-processing circuits to thereby substantially reduce the electrical noise content of said examination signals transmitted to said processor.

12. The improved method according to claim 11, wherein said sensor is disposed in contact with said patient by conforming a softly compliant component against a surface area of the patient.

13. The improved method according to claim 11, wherein said electrically conductive member is secured in contact with the patient by using conductive adhesive therebetween.

14. The improved method according to claim 13, wherein said conductive member and said sensor are secured in contact with said patient by using adhesive therebetween.

* * * * *